United States Patent [19]

Elbe

[11] 4,380,628
[45] Apr. 19, 1983

[54] PROCESS FOR THE PREPARATION OF AZOLYL-VINYL KETONES

[75] Inventor: Hans-Ludwig Elbe, Wuppertal, Fed. Rep. of Germany

[73] Assignee: Bayer Aktiengesellschaft, Leverkusen, Fed. Rep. of Germany

[21] Appl. No.: 219,154

[22] Filed: Dec. 22, 1980

[30] Foreign Application Priority Data

Jan. 10, 1980 [DE] Fed. Rep. of Germany ....... 3000643

[51] Int. Cl.³ .................. C07D 233/61; C07D 249/08
[52] U.S. Cl. ..................................... 542/429; 542/428;
542/400; 542/416; 542/427; 542/453; 542/457;
542/458; 542/467; 542/468; 542/470; 542/471;
542/472; 542/473; 548/262; 548/336; 548/341;
424/269; 424/273 R
[58] Field of Search ............... 542/429, 428, 416, 427,
542/453, 467, 457, 471, 458, 470; 548/262, 341,
336

[56] References Cited

FOREIGN PATENT DOCUMENTS

| 5600 | 11/1978 | European Pat. Off. . |
| 2331 | 6/1979 | European Pat. Off. . |
| 2645617 | 8/1976 | Fed. Rep. of Germany . |
| 2726043 | 12/1977 | Fed. Rep. of Germany . |
| 2652313 | 5/1978 | Fed. Rep. of Germany . |
| 2838847 | 3/1979 | Fed. Rep. of Germany . |
| 2826760 | 1/1980 | Fed. Rep. of Germany . |

*Primary Examiner*—Alton D. Rollins
*Attorney, Agent, or Firm*—Sprung, Horn, Kramer & Woods

[57] ABSTRACT

An azolyl-vinyl ketone of the formula

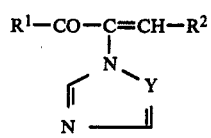

in which

Y is N or CH, and $R^1$ and $R^2$ are various organic radicals, is produced by reacting the novel keto-enamine of the formula

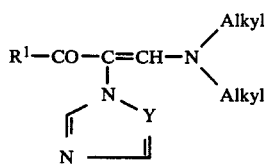

with an organometallic compound of the formula $Z-R^2$ in which Z represents the group Hal-Mg or an alkali metal or the grouping $LiCuR^2$, and Hal represents halogen, in the presence of a solvent. The end products, some of which are known, are fungicidally active.

15 Claims, No Drawings

PROCESS FOR THE PREPARATION OF AZOLYL-VINYL KETONES

The present invention relates to a novel process for the preparation of certain azolyl-vinyl ketones, some of which are known, which have fungicidal properties.

It has already been disclosed that azolyl-vinyl ketones of the general formula

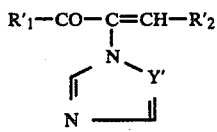  (I)

in which
- Y' represents a nitrogen atom or the CH group,
- R'$_1$ represents optionally substituted phenyl and
- R'$_2$ represents optionally substituted phenyl, alkyl, furyl or thienyl (see German Published Specification DOS Pat. No. 2,645,617 and U.S. Patent Specifications B 4,067,989 and 4,086,351), or
- R'$_1$ represents alkyl and
- R'$_2$ represents optionally substituted phenyl (see Japanese Patent Specification J53 130 661), are obtained when azolyl ketones of the general formula

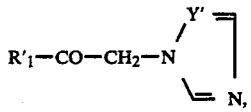  (II)

in which
- R'$_1$ and Y' have the meanings indicated above, are reacted with aldehydes of the general formula $$O=CH-R'_2 \quad (III),$$

in which
- R'$_2$ has the meaning indicated above, in the presence of a customary basic catalyst, for example sodium hydroxide, sodium carbonate, piperidine of pyridine, and in the presence of a solvent, such as, in particular, an aromatic hydrocarbon, or glacial acetic acid or acetic anhydride, at temperatures between 0° and 120° C. (see the above-mentioned patent specifications and German Published Specification DOS Pat. No. 2,838,847).

This process has the disadvantage, however, that it is not broadly applicable with respect to the substituent R'$_2$. In particular, only a few selected condensation products of the formula (I) are available for aliphatic aldehydes. Furthermore, undesired shifts in the double bond frequently occur, likewise especially when aliphatic aldehydes are employed.

The present invention now provides a process for the preparation of an azolyl-vinyl ketone of the general formula

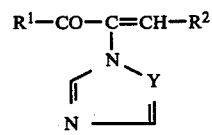  (IV)

in which
- R$^1$ represents alkyl, halogenoalkyl or optionally substituted aryl,
- R$^2$ represents alkyl, halogenoalkyl, optionally substituted aryl, an optionally substituted cycloalkyl or cycloalkenyl radical, an optionally substituted cycloalkylalkyl or cycloalkenylalkyl radical, an optionally substituted furyl or thiophenyl radical, alkoxyalkyl, alkylmercaptoalkyl, an optionally substituted alkenyl, alkynyl or alkenynyl radical, an optionally substituted indenyl or fluorenyl radical, an optionally substituted pyridinyl, thiazolyl or quinolinyl radical, an optionally substituted diphenylmethyl or triphenylmethyl radical or the grouping

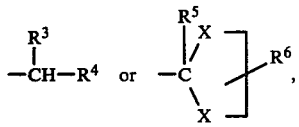

wherein
- R$^3$ represents hydrogen, cyano, alkyl, alkenyl, alkynyl or the grouping —CO$_2$R$^6$, —CONR$^7$R$^8$, —SO$_2$NR$^7$R$^8$ or —SO$_3$H,
- R$^4$ represents optionally substituted aryl, an optionally substituted pyridinyl or thiazolyl radical, an optionally substituted furyl or thiophenyl radical, an optionally substituted dioxolanyl or dithiolanyl radical, cyano or the grouping —CO$_2$R$^6$ or —SO$_2$R$^9$,
- R$^5$ represents hydrogen, alkyl, optionally substituted cycloalkyl, optionally substituted aryl or optionally substituted pyridinyl,
- R$^6$ represents hydrogen, alkyl, alkoxyalkyl or optionally substituted benzyl,
- R$^7$ and R$^8$ are identical or different and each represent alkyl,
- R$^9$ represents alkyl or optionally substituted phenyl,
- X represents oxygen or sulphur and
- Y represents nitrogen or the CH group, in which a keto-enamine of the general formula

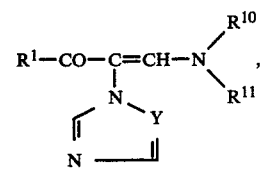  (V)

in which
- R$^1$ and Y have the meanings indicated above and
- R$^{10}$ and R$^{11}$ are identical or different and each represent alkyl, is reacted with an organometallic compound of the general formula $$Z-R^2 \quad (VI),$$

in which
R² has the meaning indicated above and
Z represents the group Hal-Mg or an alkali metal or the grouping LiCuR²,
wherein
Hal represents halogen and
R² has the meaning indicated above,
in the presence of a solvent.

The compounds of the formula (IV) can exist in the form of two geometric isomers (E-form and Z-form), depending on the arrangement of the groups bonded to the double bond; they are preferably obtained in a varying ratio of E- and Z-isomers.

It is surprising that the reaction according to the invention proceeds in the manner indicated. The reaction of the organometallic compounds with the carbonyl group of the ketoenamine, which would be expected and is observed in many other cases, does not take place. It is likewise surprising that undesired shifts of the double bond do not take place.

The process according to the invention has a number of advantages. Thus, all the compounds, both of the triazole series and of the imidazole series, are producible in good yields, there being no very great restriction with regard to the substituent R². Undesired shifts of the double bond, such as are to be observed relatively frequently in the case of known aldol reactions, especially with aliphatic aldehydes, do not take place, which leads to a simpler isolation and a higher yield of the desired product of the formula (IV).

The formula (IV) provides a general definition of the azolylvinyl ketones which can be prepared by the process according to the invention. Preferably, in this formula, R¹ represents straight-chain or branched alkyl with 1 to 6 carbon atoms, straight-chain or branched halogenoalkyl with 1 to 4 carbon atoms and 1 to 5 identical or different halogen atoms (especially, fluorine, chlorine and bromine atoms) or aryl which has 6 to 10 carbon atoms (especially phenyl or naphthyl) and optionally carries one or more substituents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms (preferred halogens being fluorine and chlorine), cyano, nitro, optionally halogen-substituted phenyl and optionally halogen-substituted phenoxy, R² represents straight-chain or branched alkyl with 1 to 12 carbon atoms; straight-chain or branched halogenoalkyl with 1 to 4 carbon atoms and 1 to 5 identical or different halogen atoms (especially fluorine, chlorine and bromine atoms);aryl which has 6 to 10 carbon atoms (especially phenyl or naphthyl) and optionally carries one or more substituents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms (preferred halogens being fluorine and chlorine), cyano, nitro, optionally halogen-substituted phenyl and optionally halogen-substituted phenoxy; cycloalkyl with 3 to 7 carbon atoms or cycloalkenyl with 5 to 7 carbon atoms, in either case optionally substituted by alkyl with 1 to 4 carbon atoms; cycloalkylalkyl which has 3 to 7 carbon atoms in the cycloalkyl part and 1 to 4 carbon atoms in the straight-chain or branched alkyl part and is optionally substituted by alkyl with 1 to 4 carbon atoms; cycloalkenylalkyl which has 5 to 7 carbon atoms in the cycloalkenyl part and 1 to 4 carbon atoms in the straight-chain or branched alkyl part and is optionally substituted by alkyl with 1 to 4 carbon atoms; furyl or thiophenyl which in either case is optionally substituted by halogen or straight-chain or branched alkyl with 1 to 4 carbon atoms; alkoxyalkyl or alkylmercaptoalkyl with in either case 1 to 4 carbon atoms in each alkyl part; optionally substituted straight-chain or branched alkenyl, alkynyl or alkenynyl with in each case up to 6 carbon atoms, the substituents being selected from hydroxyl, alkoxy with 1 to 4 carbon atoms and phenyl which is optionally substituted by halogen; indenyl or fluorenyl which in either case is optionally substituted by halogen, alkyl with 1 to 4 carbon atoms or alkoxy with 1 to 4 carbon atoms; thiazolyl, pyridinyl or quinolinyl which in each case is optionally substituted by alkyl with 1 to 4 carbon atoms or alkoxy with 1 to 4 carbon atoms; diphenyl- or triphenyl-methyl, wherein each phenyl optionally carries one or more substitutents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms (preferred halogens being fluorine and chlorine), cyano, nitro, optionally halogen-substituted phenyl and optionally halogen-substituted phenoxy, or the grouping

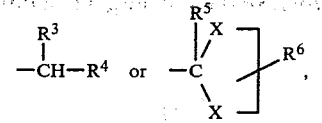

R³ represents hydrogen, cyano, straight-chain or branched alkyl with 1 to 4 carbon atoms, alkenyl or alkynyl with in either case 2 to 4 carbon atoms, or the grouping —CO₂R⁶, —CONR⁷R⁸, —SO₂NR⁷R⁸ or —SO₃H, R⁴ represents aryl which has 6 to 10 carbon atoms (especially phenyl or naphthyl) and optionally carries one or more substituents selected from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms (preferred halogens being fluorine and chlorine), cyano, nitro, optionally halogen-substituted phenyl and optionally halogen-substituted phenoxy; pyridinyl or thiazolyl which in either case is optionally substituted by alkyl with 1 to 4 carbon atoms or alkoxy with 1 to 4 carbon atoms; furyl or thiophenyl which in either case is optionally substituted by halogen or alkyl with 1 to 4 carbon atoms; dioxolanyl or dithiolanyl which in either case is optionally substituted by alkyl with 1 to 4 carbon atoms, alkoxyalkyl with 1 to 4 carbon atoms in each alkyl part or benzyl; cyano; or the grouping —CO₂R⁶ or —SO₂R⁹, R⁵ represents hydrogen; straight-chain or branched alkyl with 1 to 4 carbon atoms; cycloalkyl which has 5 to 7 carbon atoms and is optionally substituted by alkyl with 1 to 2 carbon atoms; optionally substituted aryl which has 6 to 10 carbon atoms (especially phenyl or naphthyl) and optionally carries one or more substituents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms (preferred halogens being fluorine and chlorine), cyano, nitro, optionally halogen-substituted phenyl and optionally halogen-substituted phenoxy; or pyridinyl which is optionally substituted by alkyl with 1 to 4 carbon atoms or alkoxy with 1 to 4 carbon atoms, $R^6$ represents hydrogen; straight-chain or branched alkyl with 1 to 4 carbon atoms; alkoxyalkyl with 1 to 4 carbon atoms in each alkyl part; or benzyl which optionally carries on the phenyl part one or more substituents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms (preferred halogens being fluorine and chlorine), cyano, nitro, optionally halogen-substituted phenyl and optionally halogen-substituted phenoxy, $R^7$ and $R^8$ are identical or different and each represent straight-chain or branched alkyl with 1 to 4 carbon atoms, and $R^9$ represents straight-chain or branched alkyl with 1 to 4 carbon atoms; or phenyl which optionally carries one or more substituents selected independently from halogen, straight-chain or branched alkyl with 1 to 4 carbon atoms, alkoxy and alkyl-thio with in either case 1 to 2 carbon atoms, halogeno-alkyl with up to 2 carbon atoms and up to 5 identical or different halogen atoms (preferred halogens being fluorine and chlorine), cyano, nitro, optionally halogen-substituted phenyl and optionally halogen-substituted phenoxy.

In the preferred compounds of the formula (IV), X and Y have the meanings indicated in the definition of the invention.

If, for example, 1-(2,4-dichlorophenyl)-3-dimethylamino-2-(1,2,4-triazol-1-yl)-prop-2-en-1-one and tert.-butyl-magnesium bromide are used as starting substances, the course of the reaction in the process according to the invention can be represented by the following equation:

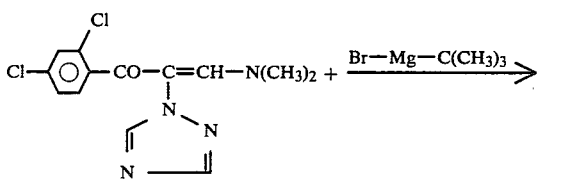

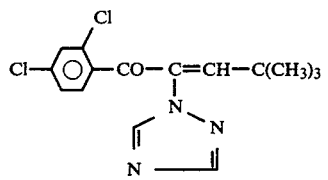

The formula (V) provides a general definition of the keto-enamines required as starting substances in carrying out the process according to the invention. In this formula, $R^1$ preferably represents those radicals which have already been mentioned as preferred therefor in connection with the description of the substances of the formula (IV) which can be prepared according to the invention. $R^{10}$ and $R^{11}$ are identical or different and preferably represent alkyl with 1 to 4 carbon atoms, especially methyl.

The keto-enamines of the formula (V) have not hitherto been described in the literature. They are obtained by reacting azolyl ketones of the general formula

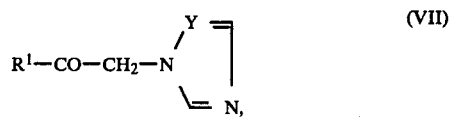

in which $R^1$ and Y have the meanings indicated above, with amide-acetals or aminal-esters of the general formula

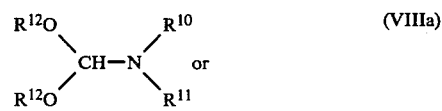

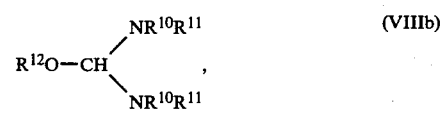

in which $R^{10}$ and $R^{11}$ have the meanings indicated above and $R^{12}$ represents alkyl with 1 to 4 carbon atoms, in a manner which is in itself known in the presence of an inert organic solvent, for example an aromatic hydrocarbon, or, in particular, an excess of the amide-acetal or aminal-ester of the formula (VIIIa) or (VIIIb) employed, at the boiling point (in this context, see also Chem. Ber. 101, 41–50 (1968); and J.Org.Chem. 43, 4,248–50 (1978) and the preparative examples given hereinafter).

The azolyl ketones of the formula (VII) are known (see U.S. Patent Application Ser. No. 792,756, filed May 2, 1977, now pending, German Published Specification DOS No. 2,610,022 and German Published Specification DOS No. 2,638,470). They can be prepared by customary methods by reacting corresponding halogeno-ketones with 1,2,4-triazole or imidazole in the presence of an acid-binding agent. (VIIIa) and (VIIIb) are generally known compounds of organic chemistry (see, for example, Chem. Ber. 101, 41–50/1968) and J.Org.-Chem. 43, 4,248–50 (1978)).

The formula (VI) provides a general definition of the organometallic compounds also to be used as starting substances for the reaction according to the invention. In this formula, $R^2$ preferably represents those radicals which have already been mentioned as preferred therefor in connection with the description of the substances of the formula (IV) which can be prepared according to the invention. Z preferably represents the group Hal-Mg, wherein Hal preferably represents chlorine or bromine. This means that the so-called "Grignard compounds", which are generally known compounds of organic chemistry, are preferably used as the organometallic compounds of the formula (VI).

If appropriate, copper complexes of the general formula $Li^{(+)} [Cu(R^2)_2]^{(-)}$ can be used as organometallic compounds of the formula (VI).

Preferred solvents for the reaction according to the invention are inert organic solvents, in the pure form or as mixtures. These solvents include, as preferences, ethers, such as diethyl ether, methyl ethyl ether, tetrahydrofuran or dioxane; alphatic and aromatic hydrocarbons, especially benzene, toluene or xylene; and hexamethylphosphoric acid triamide.

The reaction temperatures can be varied with a substantial range in carrying out the process according to the invention. In general, the reaction is carried out at between −50° and +150° C., preferably between −20° and +120° C.

In carrying out the process according to the invention, 1 to 1.5 mols of organometallic compound of the formula (VI) are preferably employed per mol of ketoenamine of the formula (V). Isolation of the compounds of the formula (IV) is effected in the customary manner.

As is known, the active compounds of the formula (IV) which can be prepared according to the invention are distinguished by a very good fungicidal activity (see German Published Specification DOS No. 2,645,617, U.S. Patent Specification Nos. 4,067,989 and 4,086,351 and Japanese Patent Specification No. J53 130 661).

The active compounds prepared according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are employed at the place of action.

The present invention also provides a fungicidal composition containing as active ingredient a compound prepared by the process of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound prepared by the process of the present invention alone or in the form of a composition containing as active ingredient such a compound in admixture with a diluent or carrier.

The present invention further provides crops protected from damage by fungi by being grown in areas in which immediately prior to and/or during the time of the growing a compound prepared by the process of the present invention was applied alone or in admixture with a diluent or carrier.

The process according to the invention is illustrated by the following preparative example:

PREPARATIVE EXAMPLE

EXAMPLE 1

(a) 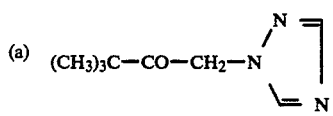

138 g (2 mol) of 1,2,4-triazole were added in portions to 276.4 g (2 mol) of ground potassium carbonate and 269.2 g (2 mol) of α-chloropinacolin in 500 ml of acetone at room temperature, during which the internal temperature rose to the boiling point. The reaction mixture was stirred under reflux for 5 hours and then cooled to room temperature. It was filtered and the filtrate was concentrated by distilling off the solvent in vacuo. The oily residue crystallized after adding benzine. 240.8 g (72% of theory) of 3,3-dimethyl-1-(1,2,4-triazol-1-yl)-butan-2-one of melting point 62°-64° C. were obtained.

(b) (i) 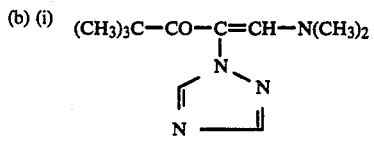 (v-i)

250.8 g (1.5 mol) of 3,3-dimethyl-1-(1,2,4-triazol-1-yl)-butan-2-one and 196 g (1.65 mol) of dimethylformamide dimethyl acetal were heated under reflux for 5 hours. Thereafter, the excess acetal was distilled off. 306 g (92% of theory) of 4,4-dimethyl-1-dimethylamino-2-(1,2,4-triazol-1-yl)-pent-1-en-3-one of refractive index $n_D^{20} 1.531$ were obtained.

(ii) 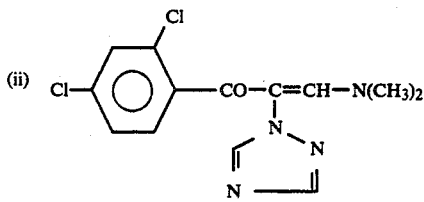 (v-ii)

266 g (1 mol) of ω-(1,2,4-triazol-1-yl)-2,4-dichloroacetophenone and 131 g (1.1 mol) of dimethylformamide dimethyl acetal were heated under reflux for 5 hours. The excess acetal was then distilled off. The oil which remained crystallized on cooling. 292 g (94% of theory) of 3-(2,4-dichlorophenyl)-1-dimethylamino-2-(1,2,4-triazol-1-yl)-prop-1-en-3-one of melting point 173° C. were obtained.

(iii) 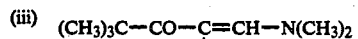 (v-iii)
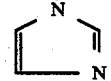

41.6 g (0.25 mol) of 3,3-dimethyl-1-(imidazol-1-yl)-butan-2-one and 35.7 g (0.3 mol) of dimethylformamide dimethyl acetal were heated under reflux for 5 hours. The excess acetal was then distilled off. The oil which remained crystallized on cooling. 50 g (90.5% of theory) of 4,4-dimethyl-1-dimethylamino-2-(imidazol-1-yl)-pent-1-en-3-one of melting point 45°–50° C. were obtained.

(c) 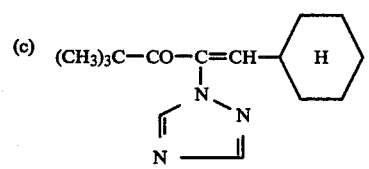 (1)

11.1 g (0.05 mol) of 4,4-dimethyl-1-dimethylamino-2-(1,2,4-triazol-1-yl)-pent-1-en-3-one were dissolved in 250 ml of ether. An ethereal solution of 13.1 g (0.07 mol) of cyclohexyl-magnesium bromide was added dropwise to this solution in the course of 30 minutes. The reaction mixture was subsequently stirred for one hour, 250 ml of water were added and the mixture was adjusted to a pH value of 6-7 with hydrochloric acid. The organic phase was separated off, dried and filtered and the filrate was concentrated. 10.8 g (83% of theory) of 1-cyclohexyl-4,4-dimethyl-2-(1,2,4-triazol-1-yl)-pent-1-en-3-one of refractive index $n_D^{20} 1.5003$ were obtained.

The following compounds of the general formula

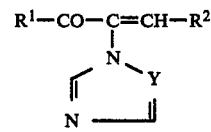 (IV)

were prepared in an analogous manner:

| Compound No. | R¹ | R² | Y | Melting point (°C.) |
|---|---|---|---|---|
| 2 | (CH₃)₃C | ⟨cyclohexenyl⟩ | N | 40–48 |
| 3 | (CH₃)₃C | ⟨cyclohexenyl-CH₃⟩ | N | 49 |
| 4 | (CH₃)₃C | —CH(C₂H₅)(C₄H₉-n) | N | Oil |
| 5 | ClCH₂—C(CH₃)₂— | ⟨cyclohexyl-H⟩ | N | 51 |
| 6 | ClCH₂—C(CH₃)₂— | ⟨cyclohexenyl⟩ | N | Oil |

-continued

| Compound No. | R¹ | R² | Y | Melting point (°C.) |
|---|---|---|---|---|
| 7 | FCH₂—C(CH₃)₂— | —CH(C₂H₅)(C₄H₉-n) | N | Oil |
| 8 | FCH₂—C(CH₃)₂— | phenyl | N | Oil |
| 9 | FCH₂—C(CH₃)₂— | cyclohexyl (H) | N | Oil |
| 10 | Cl—C₆H₄— | n-C₃H₇ | N | Oil |
| 11 | Cl—C₆H₄— | —C₆H₄—Cl | N | 185–86 |
| 12 | Cl—C₆H₄— | —C₆H₄—OCH₃ | N | 80–82 |
| 13 | Cl—C₆H₄— | thienyl (S) | N | 110–11 |
| 14 | C₆H₅— | furyl (O) | N | 108–10 |
| 15 | C₆H₅—C₆H₄— | —C₆H₄—Cl | N | 171–73 |
| 16 | Cl—C₆H₄— | —C₆H₄—Cl | CH | 117–20 |
| 17 | F—C₆H₄— | —C₆H₄—Cl | CH | 142–44 |
| 18 | C₆H₅— | —C₆H₄—F | CH | 85–86 |
| 19 | Cl—C₆H₄— | —C₆H₅ | CH | 146–49 |
| 20 | (CH₃)₃C— | —C₆H₄—O—C₆H₅ | CH | 88–90 |
| 21 | (CH₃)₃C— | —C₆H₄—Br | CH | 90–92 |
| 22 | (CH₃)₃C— | —C₆H₃(CH₃)₂ | CH | 65–70 |
| 23 | (CH₃)₃C— | —C₆H₄—Cl | N | 68 |
| 24 | (CH₃)₃C— | —C₆H₄—CH₃ | N | 65 |
| 25 | (CH₃)₃C— | —C₆H₅ | N | $n_D^{20} = 1.557$ |
| 26 | (CH₃)₃C— | —C₆H₄—OCH₃ | N | 75 |
| 27 | (CH₃)₃C— | thienyl-CH₃ | N | 95 |
| 28 | (CH₃)₃C— | —C₆H₄—F | N | $n_D^{20} = 1.5560$ |
| 29 | (CH₃)₃C— | —C₆H₄—C₆H₅ | N | 118 |
| 30 | (CH₃)₃C— | Cl-substituted phenyl | CH | 90 |
| 31 | C₆H₅—C₆H₄— | Cl-substituted phenyl | CH | 110 |

It will be understood that the specification and examples are illustrative but not limitative of the present invention and that other embodiments within the spirit and scope of the invention will suggest themselves to those skilled in the art.

I claim:

1. A process for the preparation of an azolyl-vinyl ketone of the formula

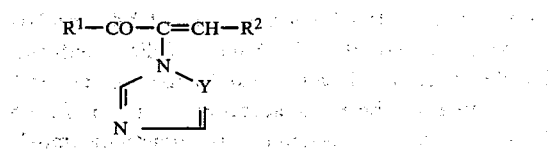

in which

R¹ represents straight-chain or branched alkyl with 1 to 6 carbon atoms, straight-chain or branched halogenoalkyl with 1 to 4 carbon atoms and 1 to 5 identical or different halogen atoms, or aryl which has 6 to 10 carbon atoms and optionally carries one or more substituents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms, cyano, nitro, optionally halogen-substituted phenyl and optionally halogen-substituted phenoxy, R² represents straight-chain or branched alkyl with 1 to 12 carbon atoms; straight-chain or branched halogenoalkyl with 1 to 4 carbon atoms and 1 to 5 identical or different halogen atoms; aryl which has 6 to 10 carbon atoms and optionally carries one or more substituents selected independently from halogen, straight-chain or branched alkyl with 1 to 4 carbon atoms, halogenoalkyl with up to 2 carbons atoms and up to 5 identical or different halogen atoms, cyano, nitro, optionally halogen-substituted phenyl and optionally halogen-substituted phenoxy; cycloalkyl with 3 to 7 carbon atoms or cycloalkenyl with 5 to 7 carbon atoms, in either case optionally substituted by alkyl with 1 to 4 carbon atoms; cycloalkylalkyl which has 3 to 7 carbon atoms in the cycloalkyl part and 1 to 4 carbon atoms in the straight-chain or branched alkyl part and is optionally substituted by alkyl with 1 to 4 carbon atoms; cycloalkenylalkyl which has 5 to 7 carbon atoms in the cycloalkenyl part and 1 to 4 carbon atoms in the straight-chain or branched alkyl part and is optionally substituted by alkyl with 1 to 4 carbon atoms; furyl or thiophenyl which in either case is optionally substituted by halogen or straight-chain or branched alkyl with 1 to 4 carbon atoms; alkoxyalkyl or alkylmercaptoalkyl with in either case 1 to 4 carbon atoms in each alkyl part; optionally substituted straight-chain or branched alkenyl, alkynyl or alkenynyl with in each case up to 6 carbon atoms, the substituents being selected from hydroxyl, alkoxy with 1 to 4 carbon atoms and phenyl which is optionally substituted by halogen; indenyl or fluorenyl which in either case is optionally substituted by halogen, alkyl with 1 to 4 carbon atoms or alkoxy with 1 to 4 carbon atoms; diphenyl- or triphenyl-methyl, wherein each phenyl optionally carries one or more substitutents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms, cyano, nitro, optionally halogen-substituted phenyl and optionally halogen-substituted phenoxy; or the grouping

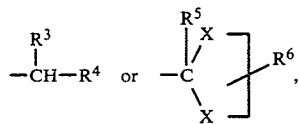

$R^3$ represents hydrogen, cyano, straight-chain or branched alkyl with 1 to 4 carbon atoms, akenyl or alkynyl with in either case 2 to 4 carbon atoms, or the grouping $-CO_2R^6$, $-CONR^7R^8$, $-SO_2NR^7R^8$ or $-SO_3H$, $R^4$ represents aryl which has 6 to 10 carbon atoms and optionally carries one or more substituents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms, cyano, nitro, optionally halogen-substituted phenyl and optionally halogen-substituted phenoxy; furyl or thiophenyl which in either case is optionally substituted by halogen or alkyl with 1 to 4 carbon atoms; dioxolanyl or dithiolanyl which in either case is optionally substituted by alkyl with 1 to 4 carbon atoms, alkoxyalkyl with 1 to 4 carbon atoms in each alkyl part or benzyl; cyano, or the grouping $-CO_2R^6$ or $-SO_2R^9$, $R^5$ represents hydrogen; straight-chain or branched alkyl with 1 to 4 carbon atoms; cycloalkyl which has 5 to 7 carbon atoms and is optionally substituted by alkyl with 1 to 2 carbon atoms; aryl which has 6 to 10 carbon atoms and optionally carries one or more substitutents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms, cyano, nitro, optionally halogen-substituted phenyl and optionally halogen-substituted phenoxy;

$R^6$ represents hydrogen; straight-chain or branched alkyl with 1 to 4 carbon atoms; alkoxyalkyl with 1 to 4 carbon atoms in each alkyl part; or benzyl which optionally carries on the phenyl part one or more substitutents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms, cyano, nitro, optionally halogen-substituted phenyl and optionally halogen-substituted phenoxy, $R^7$ and $R^8$ are identical or different and each represent straight-chain or branched alkyl with 1 to 4 carbon atoms, $R^9$ represents straight-chain or branched alkyl with 1 to 4 carbon atoms; or phenyl which optionally carries one or more substitutents selected independently from halogen, straight chain or branched alkyl with 1 to 4 carbon atoms, alkoxy and alkylthio with in either case 1 to 2 carbon atoms, halogenoalkyl with up to 2 carbon atoms and up to 4 identical or different halogen atoms, cyano, nitro, optionally halogen-substituted phenyl and optionally halogen-substituted phenoxy, comprising reacting a keto-enamine of the formula

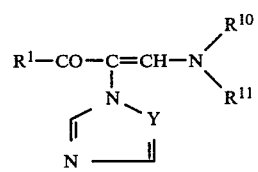

in which $R^{10}$ and $R^{11}$ are identical or different and each represent alkyl with 1 to 4 carbon atoms, with an organometallic compound of the formula $$Z-R^2$$

in which

Z represents the group Hal-Mg or an alkali metal or the grouping $LiCuR^2$, and

Hal represents halogen, in the presence of a solvent.

2. A process according to claim 1, wherein the reaction is carried out at a temperature from about $-50°$ to $+150°$ C.

3. A process according to claim 1, wherein the reaction is carried out in an inert organic solvent.

4. A process according to claim 1, wherein the solvent is an ether, an aliphatic or aromatic hydrocarbon or hexamethyl-phosphoric acid triamide.

5. A process according to claim 1, wherein about 1 to 1.5 mols of the organometallic compound are employed per mol of the keto-enamine.

6. A process according to claim 1, wherein Z is Cl-Mg or Br-Mg.

7. A process according to claim 1, wherein $R^{10}$ and $R^{11}$ are both methyl.

8. A process according to claim 4, wherein the reaction is carried out at a temperature from about $-20°$ to $+120°$ C. with about 1 to 1.5 mols of the organometallic compound per mol of the keto-enamine, Z is Cl-Mg or Br-Mg and $R^{10}$ and $R^{11}$ are both methyl.

9. A process according to claim 1, wherein $R^1$ is tert.-butyl and $R^2$ is cyclohexyl.

10. A process according to claim 1, wherein $R^1$ is p-chlorophenyl and $R^2$ is n-propyl.

11. A process according to claim 1, wherein $R^1$ is p-chlorophenyl and $R^2$ is p-chlorophenyl.

12. A process according to claim 1, wherein $R^1$ is tert.-butyl and $R^2$ is p-bromophenyl.

13. A process according to claim 1, wherein $R^1$ is tert.-butyl and $R^2$ is p-chlorophenyl.

14. A keto-enamine of the formula

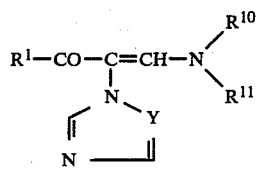

in which
$R^1$ represents, straight-chain or branched alkyl with 1 to 6 carbon atoms, straight-chain or branched halogenoalkyl with 1 to 4 carbon atoms and 1 to 5 identical or different halogen atoms or aryl which has 6 to 10 carbon atoms and optionally carries one or more substituents selected independently from halogen, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms, cyano, nitro, optionally halogen-substituted phenyl and optionally halogen-substituted phenoxy, Y is nitrogen or the CH group, and $R^{10}$ and $R^{11}$ each independently is alkyl with 1 to 4 carbon atoms.

15. A keto-enamine according to claim 14, wherein $R^1$ is tert.-butyl or p-chlorophenyl.

* * * * *

UNITED STATES PATENT AND TRADEMARK OFFICE
CERTIFICATE OF CORRECTION

PATENT NO. : 4,380,628
DATED : April 19, 1983
INVENTOR(S) : Hans-Ludwig Elber

It is certified that error appears in the above-identified patent and that said Letters Patent is hereby corrected as shown below:

On the title page

| | |
|---|---|
| Under U.S. Patents | Insert omitted patent --4291044  9/81 Jager et al  542/458 |
| Col. 4, line 44 | After "selected" insert omitted word --independently-- |
| Col. 7, line 1 | Delete "alphatic" and insert --aliphatic-- |

Signed and Sealed this

Nineteenth Day of July 1983

[SEAL]

Attest:

GERALD J. MOSSINGHOFF

Attesting Officer

Commissioner of Patents and Trademarks